United States Patent [19]

Spolyar

[11] Patent Number: 4,566,444
[45] Date of Patent: Jan. 28, 1986

[54] PORTABLE ROENTGENOGRAPHIC CEPHALOSTAT

[76] Inventor: John L. Spolyar, 2769 Homewood Dr., Troy, Mich. 48098

[21] Appl. No.: 453,949

[22] Filed: Dec. 28, 1982

[51] Int. Cl.[4] ............................................. G03B 41/16
[52] U.S. Cl. ................................ 128/303 B; 378/180; 378/178; 250/491.1
[58] Field of Search ................ 128/303 B; 378/20, 79, 378/81, 177, 178, 179, 180, 208, 162, 163; 250/491.1

[56] References Cited

U.S. PATENT DOCUMENTS

| | | | |
|---|---|---|---|
| 3,072,788 | 1/1963 | Oller | 378/178 X |
| 3,514,606 | 5/1970 | Rabey | 378/180 X |
| 3,626,186 | 12/1971 | Allard | 378/178 X |
| 3,704,707 | 12/1972 | Halloran | 378/162 X |
| 4,088,893 | 5/1978 | Schroeder | 378/180 X |
| 4,144,460 | 3/1979 | Norman | 378/180 X |
| 4,229,656 | 10/1980 | Iversen et al. | 378/178 |
| 4,256,112 | 3/1981 | Kopf et al. | 128/303 B |
| 4,341,220 | 7/1982 | Perry | 128/303 B |

Primary Examiner—Edward M. Coven
Attorney, Agent, or Firm—Lon H. Romanski

[57] ABSTRACT

A portable cephalostat is shown as having a frame-like base subassembly which provides for an area upon which a patient's head is to rest and a support for supporting locating arms which serve to locate the patient's head in a selected position; the base subassembly provides for the placement of a first film, to be exposed, below the patient's head and for the placement of additional film, also to be exposed, generally to one side of the patient's head and generally parallel to the midsagittal plane of the patient's head; and a dial indicator is provided for, upon attaining the desired location of the patient's head, automatically indicating the elevation of the axis of the patient's auditory canals with respect to the first film.

13 Claims, 19 Drawing Figures

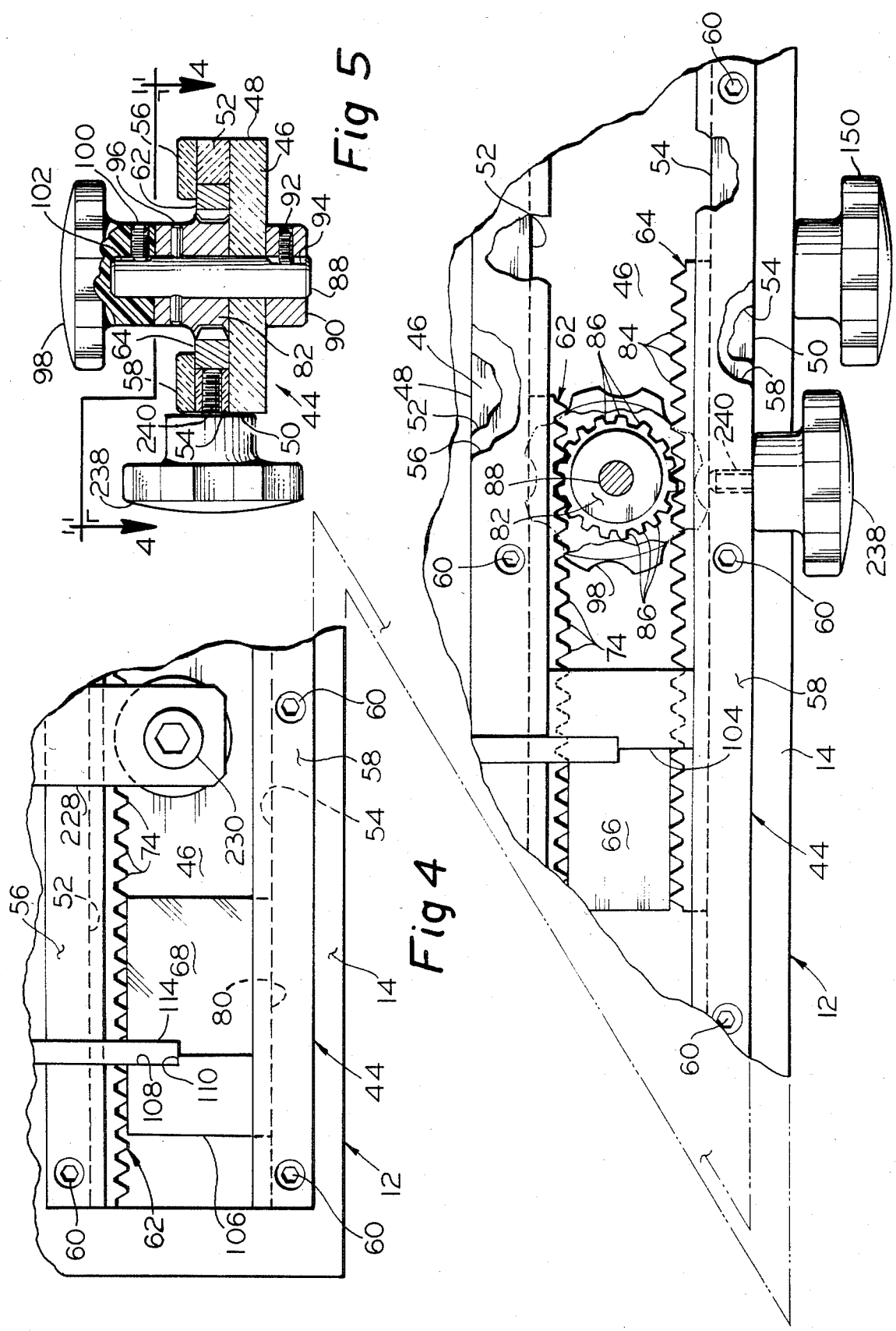

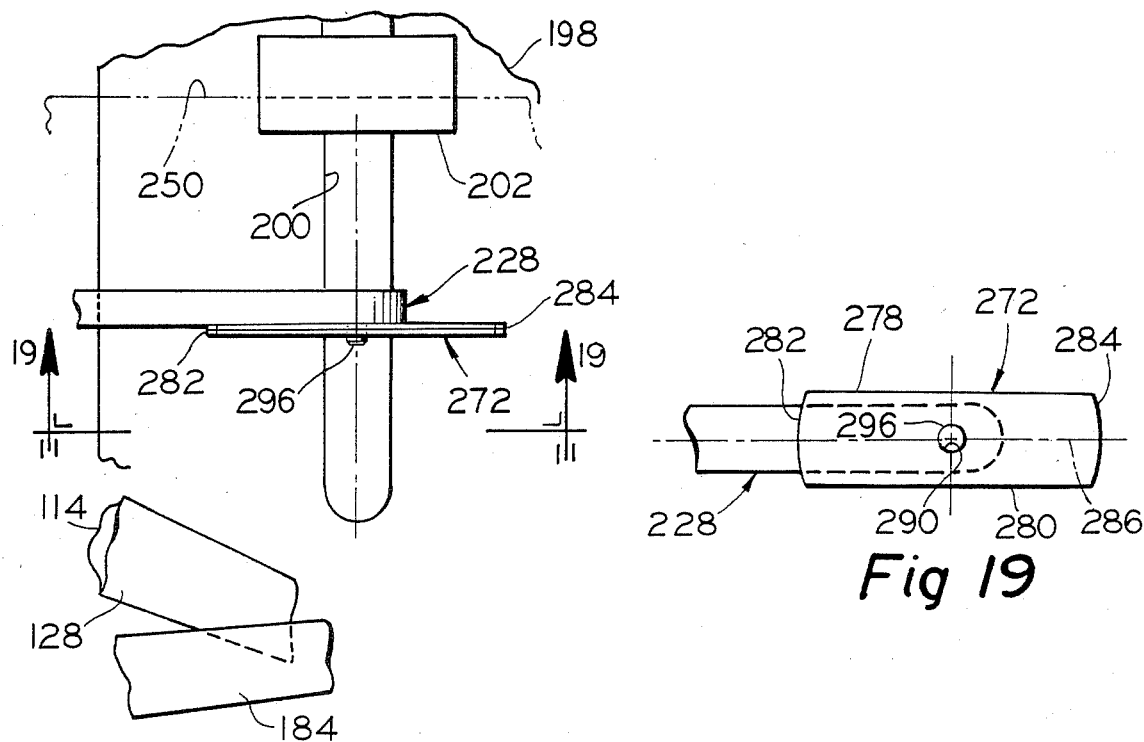
Fig 18
Fig 19
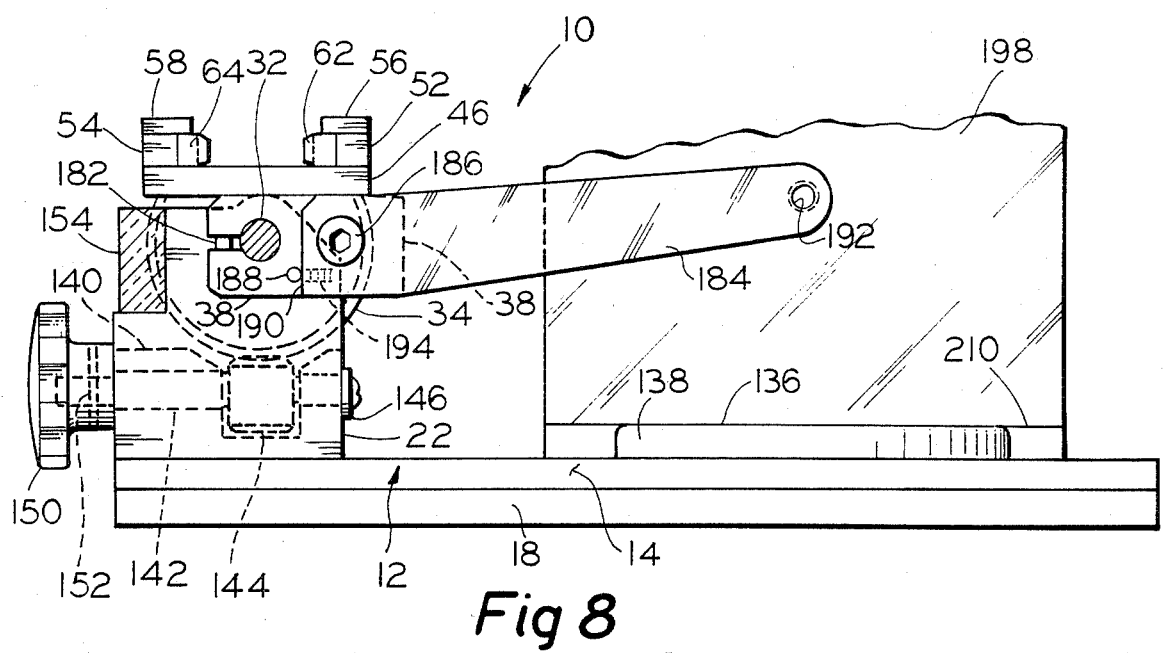
Fig 8

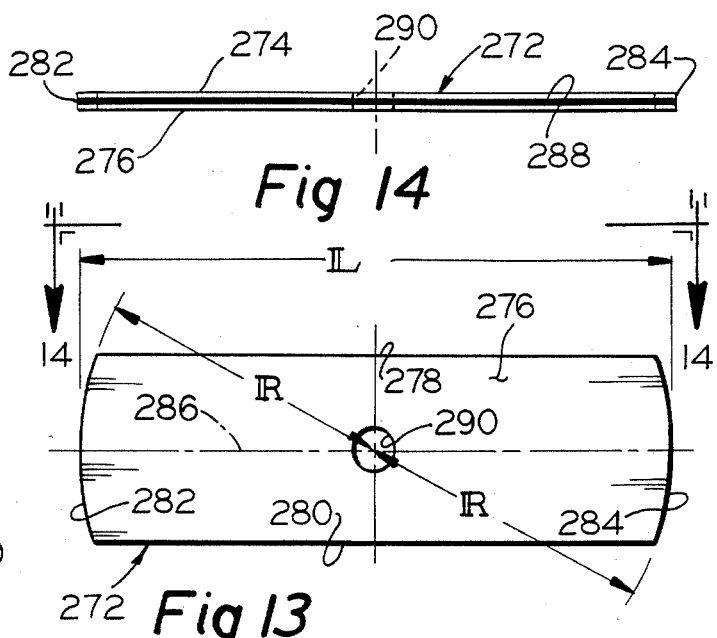
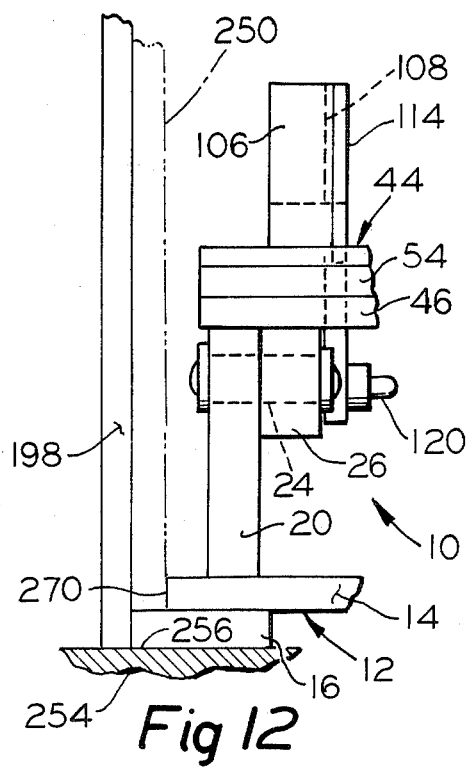
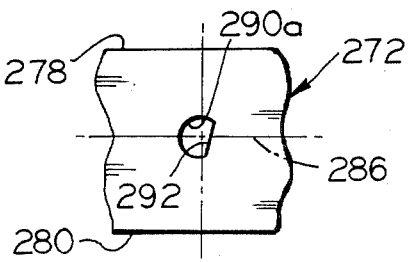
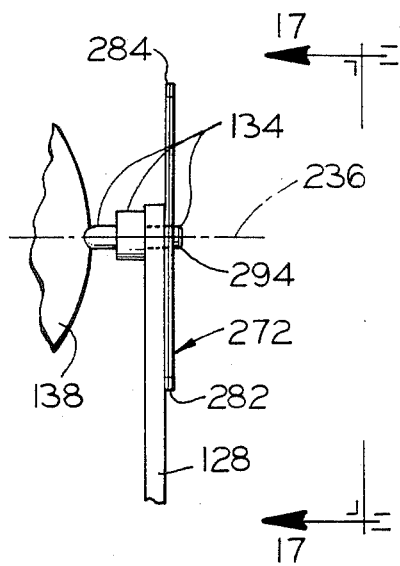
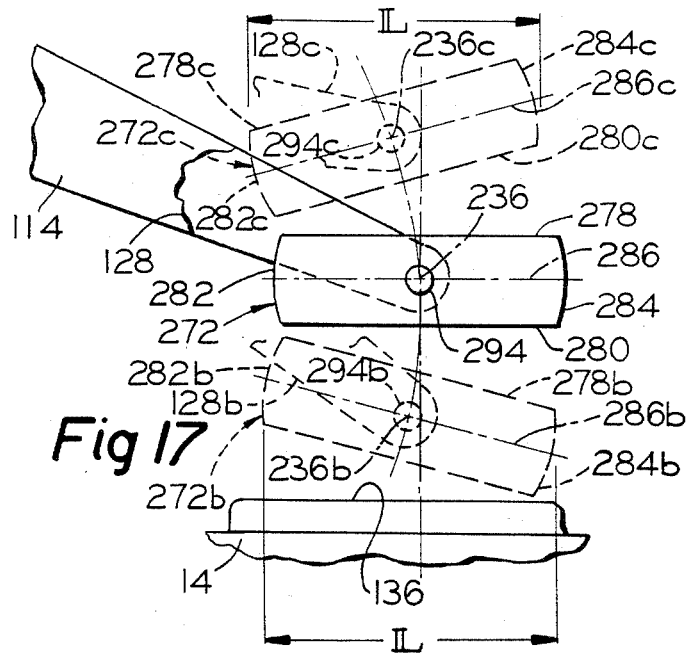

4,566,444

PORTABLE ROENTGENOGRAPHIC CEPHALOSTAT

FIELD OF THE INVENTION

This invention relates generally to cephalostatic apparatus and more particularly to such apparatus which is portable and enables the production of both lateral and anterior-posterior cephlograms which are reproducible in terms of image magnification and degree of distortions.

BACKGROUND OF THE INVENTION

Heretofore many occasions have arisen where it was at least highly desirable to produce a cephlogram which would have the quality of reproducibility. For example, in the case of orthodontic procedures it is necessary to be able to produce cephlograms, spaced in time, to determine the degree of correction obtained by the prodecures employed. If the patient is an infant, or unable to stand or sit in order to be able to have such cephlograms taken by conventional x-ray units designed for this purpose, the practitioner is, more often than not, unable to obtain the required cephalostatic cephlograms and must rely, in the main, upon the visual appearance of the patient or variably magnified and distorted cephalograms which, of course, may be deceiving of the actual situation.

In the instances of oral surgery, for example, if surgery were being performed on the jaw, it would be a distinct advantage for the surgeon to be able to determine the jaw configuration while the patient was still on the operating table. However, the prior art does not provide apparatus permitting such cephlograms grams to be taken of the patient while still on the operating table.

Further, in cases of cranial surgery, especially where the cranial bone is cut-off during the procedure, as, for example in infants and young children, for the remediation of early cranial suture closure, it would be of great advantage to the surgeon. That is, it is not uncommon in such procedures to insert bone markers on either side of a bone cut and to periodically thereafter take radiograms to see if the spacing between such bone markers, as well as naturally occuring land marks, has increased indicating displacement growth in the cranial system. It would be of material advantage to the surgeon if a pre-surgical and post-surgical cephlogram could be obtained showing the bone markers and cranial structures while the patient is still on the operating table. Also, such radiograms are difficult to obtain during the patient's convalescence due to patient age and need for sedation to obtain them. Again, the prior art does not provide apparatus enabling such cephlograms to be taken of the patient while still on the operating table or in an X-ray department under sedation.

In all of such exemplory situations, among others, the purpose of the cephlogram is to be able to study and determine changes, occurring over a significant span of time, in primarily, the bone structure of the patient. In order to be able to compare a series of such (spaced-in-time) cephlograms, and from that accurately determine what if any changes have occurred, and if occurred, the degree thereof, all variables must be eliminated in the process of obtaining each cephlogram. The prior art has failed to provide such apparatus with such capabilities which, further, could be employed in obtaining cephlograms of infants, invalids incapable of either standing or sitting, or of patients still on the operating table.

The invention as herein disclosed is directed generally to the solution of the above and other related and attendant problems of the prior art.

SUMMARY OF THE INVENTION

According to the invention, a cephalostat comprises portable frame means, means for locating the back of a patient's head at a reference plane of elevation, means for locating first unexposed film at a selected elevation below the back of the patient's head and at a preselected elevation below said plane of elevation, means for locating second unexposed film to one side of the patient's head when the back of said patient's head is located against said reference plane of elevation, mechanically adjustable means for guidingly positioning said patient's head along said reference plane of elevation as to thereby place said patient's head as to have the mid-sagittal plane of said patient's head situated at a preselected distance from said second unexposed film, and means for indicating the elevation above said reference plane of elevation of the patient's auditory canals.

Various general and specific objects, advantages and aspects of the invention will become apparent when reference is made to the following detailed description considered in conjunction with the accompanying drawings.

BRIEF DESCRIPTION OF THE DRAWINGS

In the drawings, wherein for purposes of clarity certain details and/or elements may be omitted from one or more views:

FIG. 4 is a relatively enlarged fragmentary portion of the structure shown in FIG. 1, with portions thereof broken away and other portions sectioned generally on a plane of line 4—4 of FIG. 5;

FIG. 5 is a relatively enlarged cross-sectional view taken generally on the plane of line 5—5 of FIG. 2 and looking in the direction of the arrows;

FIG. 8 is a relatively enlarged, generally cross-sectional view, taken generally on the plane of line 8—8 of FIG. 1 and looking in the direction of the arrows;

FIG. 12 is a view corresponding to a fragmentary portion of the structure shown in FIG. 1 and illustrating a modification thereof;

FIG. 13 is an elevational view of an element employable in combination with the structure of FIGS. 1-12;

FIG. 14 is an elevational view taken generally on the plane of line 14—14 of FIG. 13 and looking in the direction of the arrows;

FIG. 15 is an elevational view of a fragmentary portion of the structure of FIGS. 13 and 14 and illustrating a modification thereof;

FIG. 16 is an elevational view of a fragmentary portion of certain of the elements shown in, for example, FIG. 1 employing in combination therewith the structure of FIGS. 13 and 14;

FIG. 17 is an elevational view taken generally on the plane of line 17—17 of FIG. 16 and looking in the direction of the arrows;

FIG. 18 is an elevational view of a fragmentary portion of certain of the elements shown in, for example, FIG. 3 employing in combination therewith the structure of FIGS. 13 and 14; and FIG. 19 is an elevational view taken generally on the plane of line 19—19 of FIG. 18 and looking in the direction of the arrows.

DETAILED DESCRIPTION OF THE INVENTION

Figure 1:
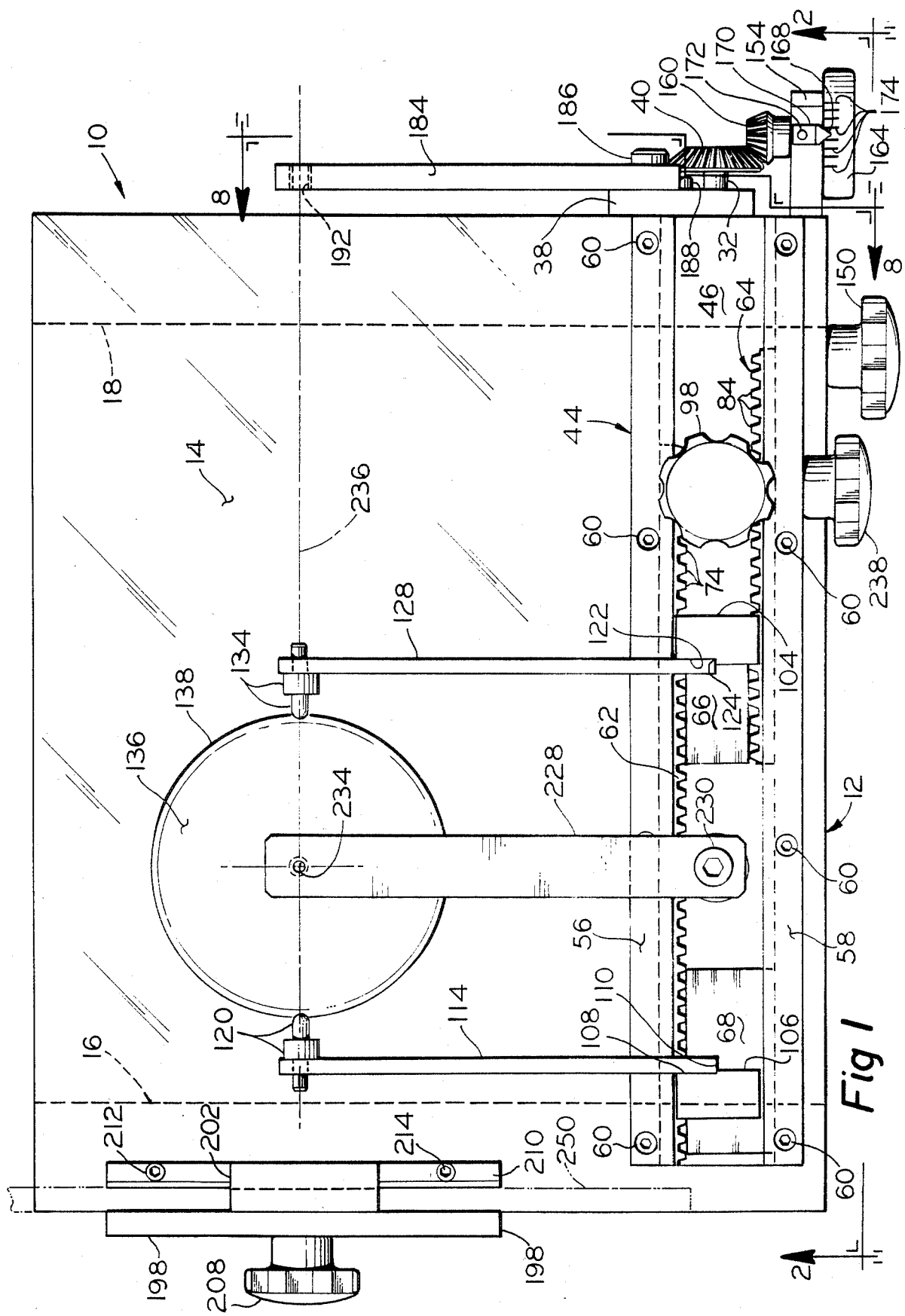
FIG. 1 is a top plan view of a cephalostat employing teachings of the invention.
Figure 2:
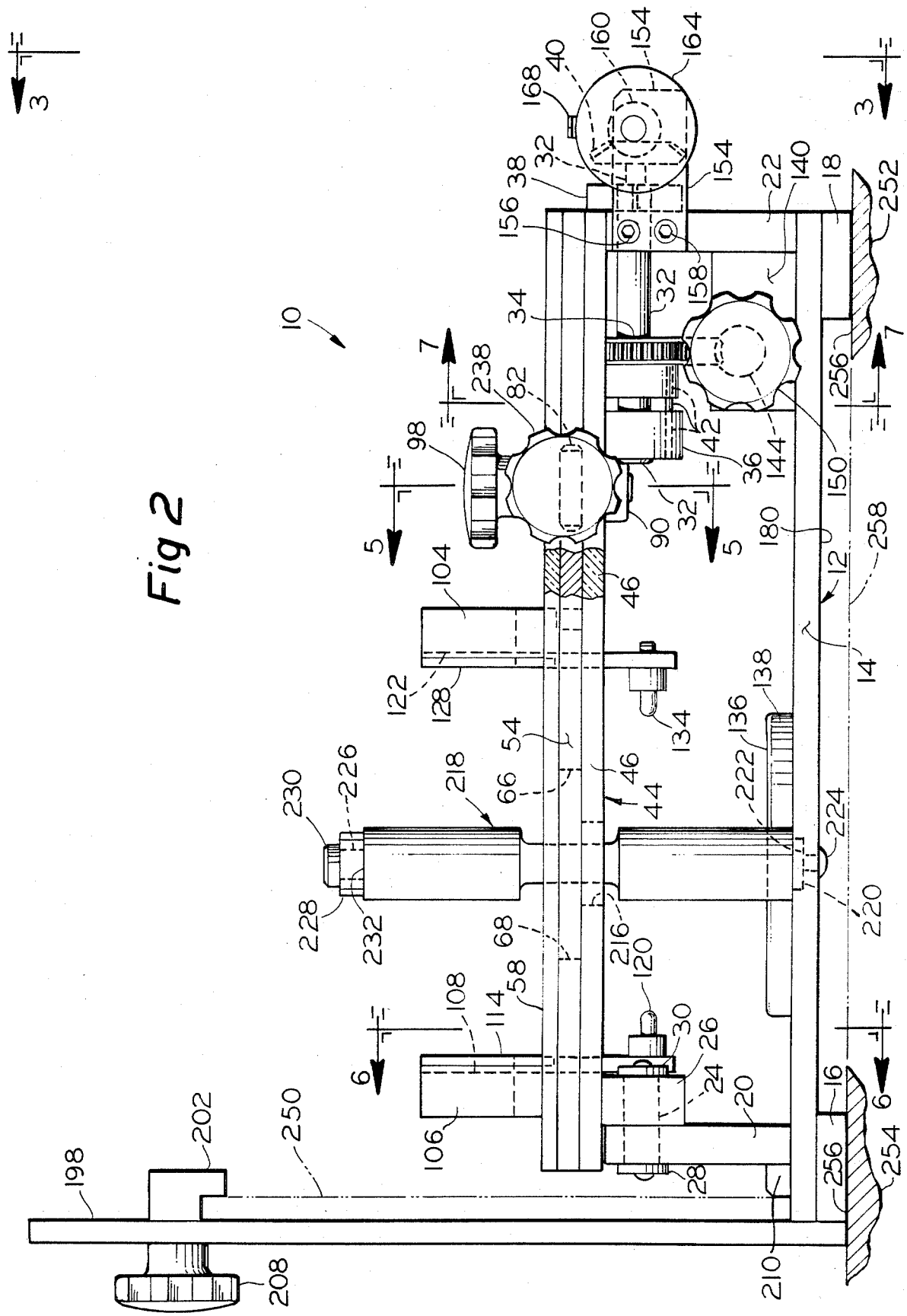
FIG. 2 is a front elevational view taken generally on the plane of line 2—2 of FIG. 1 and looking in the direction of the arrows.
Figure 3:
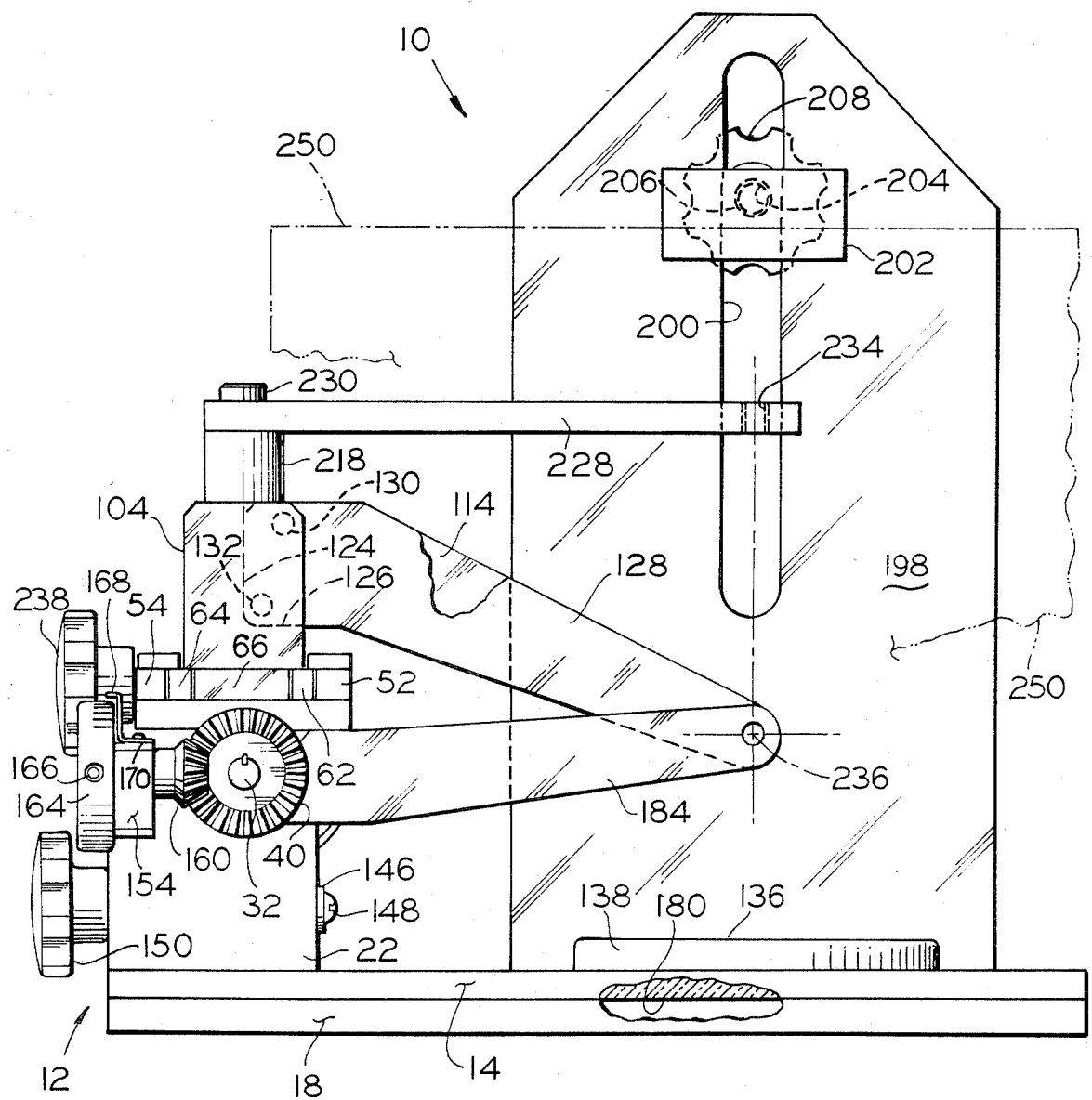
FIG. 3 is an end elevational view taken generally on the plane of line 3—3 of FIG. 2 and looking in the direction of the arrows.

Referring now in greater detail to the drawings, and in particular to FIGS. 1, 2 and 3, the cephalostat 10 of the invention is illustrated as comprising frame or support means 12 which, in turn, preferably comprises a generally rectilinear plate-like base 14 which is supported as by parallel spaced legs, risers or feet 16 and 18 which may be integrally formed with or suitably secured to the base 14 by any suitable means such as screws (not shown).

Figure 6:
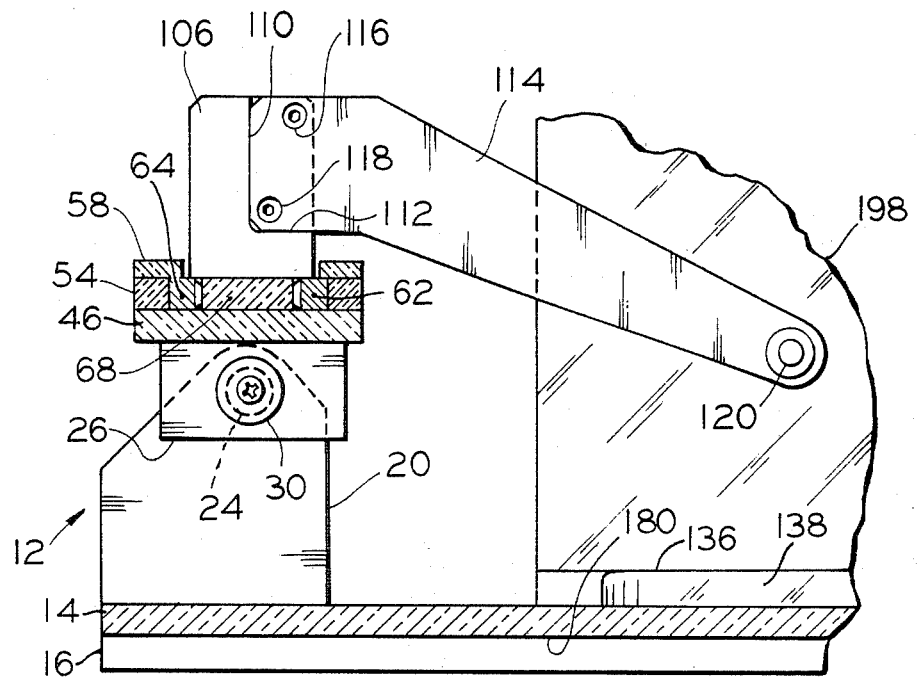
FIG. 6 is a relatively enlarged, generally cross-sectional view, taken generally on the plane of line 6—6 of FIG. 2 and looking in the direction of the arrows.

The frame or support means 12 further comprises a pair of generally oppositely disposed trunnion-like or pivot support members 20 and 22 which may be formed of any suitable material but preferably are formed of metal such as, for example, steel. Such pivot support members 20 and 22 may be secured to the base plate 14 in any suitable manner as by, for example, screws (not shown). As shown in FIGS. 2 and 6, the support or leg member 20 carries a pivot pin or journal 24 which, in turn, pivotally extends through and supports an associated support block 26. Suitable end thrust washers or the like 28 and 30 may be provided as to axially contain the pivot pin 24.

Referring in particular to FIGS. 2, 3 and 8, the support or leg member 22 is shown as pivotally carrying a shaft 32 which, as best seen in FIG. 2, extends to the left (as viewed in FIG. 2) of support member 22 and through worm wheel means 34 and associated support and drive block means 36. As seen in each of FIGS. 1 and 2, the shaft means 32 extends to the right (as viewed in either FIGS. 1 or 2) of support member 22 through a lever or arm member 38 and operatively into a bevel gear 40 cooperatively secured thereto for rotation in unison therewith.

In the preferred arrangement, the worm gear 34 and hub portion are pressed or keyed onto shaft means 32 so that rotation of worm gear 34 causes like rotation of the shaft means 32. As best shown in FIG. 2, the worm gear 34 and support block means 36 are operatively rigidly interconnected to each other as by a drive pin or drive dog means 42 thereby resulting in rotation of the drive block means 36 about the axis of shaft means 32 corresponding to the degree of rotation of worm gear 34. Both blocks 26 and 36 are suitably fixedly secured, as by, for example, screws (not shown) to the inclinable platform assembly 44 thereabove.

Referring primarily to FIGS. 1, 2, 4 and 5, the inclinable platform assembly 44 is illustrated as comprising a lower disposed generally rectilinear longitudinally extending base plate member 46 having opposed longitudinal edges 48 and 50 generally along which are situated guides or ways 52 and 54, respectively. Situated generally atop the ways 52 and 54 are respective elogated keeper members 56 and 58, each of a transverse width slightly greater than the ways 52 and 54. The keepers, ways and base plate 46 may all be secured to each other, to form a unitary structure, as by screws 60.

A first gear rack 62 is slidably nested against way 52 and between upper keeper 56 and lower plate or platform 46 as to be slidable longitudinally therealong. A second gear rack 64 is similarly slidably nested against way 54 and between upper keeper 58 and lower plate or platform 46 as to be slidable longitudinally therealong.

Figure 9:
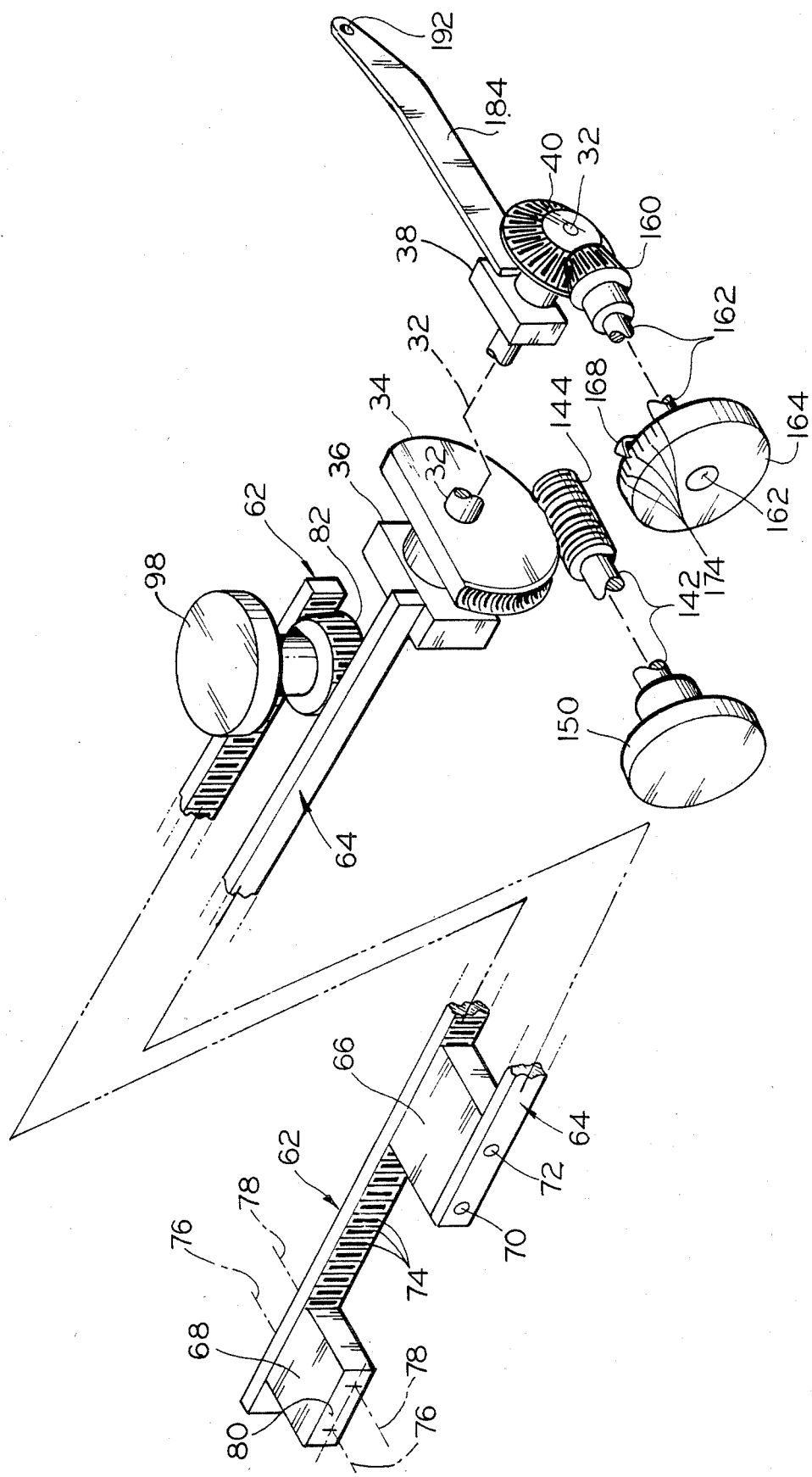
FIG. 9 is a somewhat simplified perspective view of a portion of the operating mechanism shown in FIGS. 1, 2 and 3.

As illustrated in, for example, FIGS. 1, 4 and 9 a pair of sliding guide and support blocks 66 and 68 are provided. Slide block 66, sliding against the platform-like plate 46, is suitably fixedly secured to gear rack 64, preferably by screws 70 and 72 as to thereby move in unison with gear rack 64. In the preferred arrangement, the thickness of slide block 66 is substantially that of the width of the gear racks 64 and 62 and, further, the width of slide 66 is such as to permit sliding motion as between the teeth 74 of gear rack 62 and the juxtaposed surface of slide 66 whenever such experience relative motion, in, of course, the assembled state depicted as in, for example, FIGS. 1 or 4.

Similarly, slide block 68, sliding against the platform-like plate 46, is suitably fixedly secured to gear rack 62, preferably by screws entering first through rack 62 and then into slide body 68 with their respective centerlines depicted at 76 and 78 as to thereby move in unison with gear rack 62. In the preferred arrangement, the thickness of slide body 68 is substantially that of the width of the gear racks 62 and 64 and, further, the width of slide 68 is such as to permit sliding motion as between side or edge 80 of slide 68 and the juxtaposed way 54.

Accordingly, in view of the above, it can be seen that functionally gear rack 64 and slide body 66 are a unitary structure and that when gear rack 64 is made to move longitudinally, slide body 66 moves correspondingly in unison therewith. Further, the same applies to gear rack 62 and slide body 68; that is, such comprise a functionally unitary structure and that when gear rack 62 is made to move longitudinally, slide body 68 moves correspondingly in unison therewith.

Referring in greater detail to FIGS. 1, 2, 4, 5 and 9, the manner in which such gear racks 62 and 64 are made to move is through a manually actuated gear 82. As best seen in FIGS. 4 and 5, gear 82 is placed as in axially abutting relationship with the top surface of platform plate 46 as to have its teeth 86 in operative engagement, at diametrically opposite sides, with the teeth 74 of gear rack 62 and the teeth 84 of gear rack 64. A drive shaft 88 extends through the gear 86 and projects some distance downwardly below the platform plate 46 where a collar-like thrust member 90 is fixedly secured thereto as by a set screw 92 cooperating with either a flatted or axially relieved portion 94 formed in shaft 88. A press-fitted cross pin 96 extends through shaft 88 and the hub of gear 82 as to thereby cause said shaft 88 and gear 82 to be functionally unitary whereby any rotation of shaft 88 results in the contemporaneous rotation of gear means 82. A manually actuatable knob 98, received generally about the upper end of shaft 88 is fixedly secured thereto, against relative rotation as by a set screw 100 and cooperating flatted portion 102 formed on shaft 88. Accordingly, when viewed in either FIGS. 1, 4 or 9, whenever knob 98 is rotated counter-clockwise gear rack 62 and slide body 68 move to the left while gear rack 64 and slide body 66 move to the right; conversely, whenever knob 98 is rotated clockwise, gear rack 62 and slide body 68 move to the right while gear rack 64 and slide body 66 move to the left.

Consequently, it can be seen, that as knob or control 98 is rotated counter-clockwise, slide blocks or bodies 68 and 66 move linearly away from each other whereas when control means 98 is rotated clockwise, slide blocks or bodies 68 and 66 move linearly toward each other.

It should now be pointed out that the purpose of such slide bodies or blocks 66 and 68 is to support and carry respective support arm members 104 and 106, respectively.

In the construction of the preferred embodiment, such support arm members are fixedly secured to the slide bodies 66 and 68, respectively, prior to the assembly of such slide bodies into and generally between ways 52 and 54. More particularly, referring to FIG. 6, and FIGS. 1, 2 and 4, the arm member 106 is illustrated as being situated atop slide body 68, and secured thereto as by a pair of screws (not shown but preferably) extending upwardly from countersunk holes in slide body 68 and into arm member 106 to thereby fixedly secure each to the other and make such secured elements effectively of unitary structure. In the preferred embodiment, the width of arm support 106 is such as to somewhat overlie and slide upon the gear racks 64 and 62. Further, in the preferred embodiment, support arm 106 is formed as with a vertically extending milled surface 108 which has a vertically extending edge-like surface 110 and a horizontally extending edge-like surface 112. Such milled (or otherwise formed) surface 108 then receives thereagainst a generally cantilevered locating arm member 114 which is preferably fixedly secured to the support arm 106, against surface 108, and generally confined by surfaces 110 and 112, as by a plurality of screws 116 and 118. The free end of locating arm 114 fixedly carries a generally cylindrical locating plug 120 of a preselected effective overall length.

Support arm 104, similarly, is situated atop slide body 66, and secured thereto as by a pair of screws (not shown but preferably) extending upwardly from countersunk holes in slide body 66 and into arm member 104 to thereby fixedly secure each to the other and make such secured elements effectively of unitary structure. Aside from this, the arm member 104 may be considered the mirror image of arm 106 and the various milled (or otherwise formed) surfaces corresponding to 108, 110 and 112 of arm 106 find their respective counterparts as at 122, 124 and 126.

Also, similarly, support arm 104 is of a width as to somewhat overlie and slide upon the gear racks 64 and 62. Such milled (or otherwise formed) surface 122 then receives thereagainst a generally cantilevered locating arm member 128 which is preferably fixedly secured to the support arm 104, against surface 122, and confined by surfaces 124 and 126, as by a plurality of screws 130 and 132. The free end of locating arm 128 carries a locating member 134 of preselected effective length which, preferably, is the same as that of locator 120.

The entire platform assembly 44 can be pivotally rotated about the aligned axes of pivot pin 24 and shaft means 32 and in so doing the height of the aligned centerlines of locators 120 and 134 is effectively raised or lowered relative to the reference plane 136 comprising the top surface of the head riser or locator member 138 upon which the back of the patient's head is to rest. Of course, such upward and downward movement of the locators 120 and 134 is in an arcuate path with the radius of such arcuate path being the distance from the aligned axes of pivot pin 24 and shaft means 32 to the aligned axes of locators 120 and 134.

Figure 7:
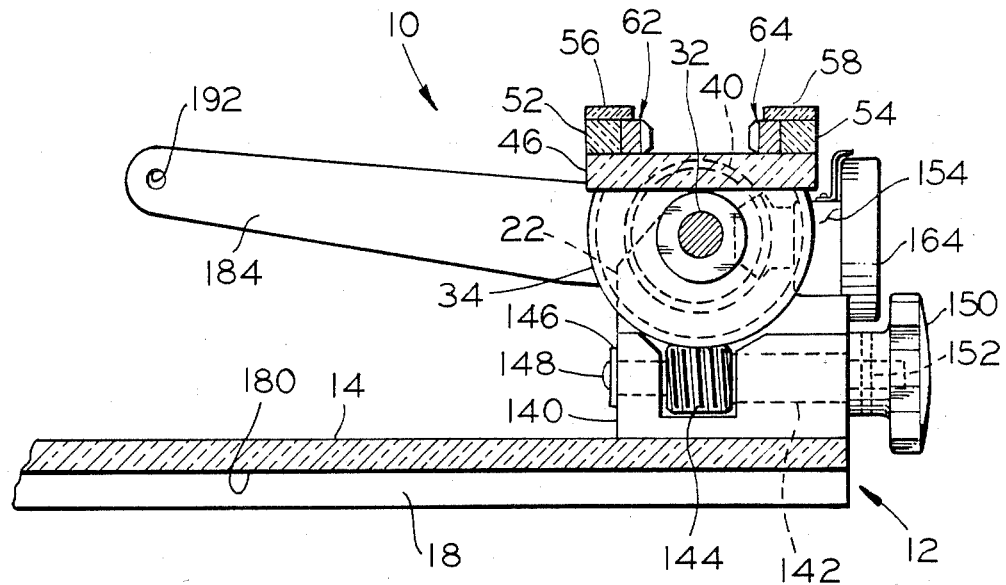
FIG. 7 is a relatively enlarged, generally cross-sectional view, taken generally on the plane of line 7—7 of FIG. 2 and looking in the direction of the arrows.

Referring primarily to FIGS. 2, 7 and 9, the manner and means by which the platform assembly 44 is controllably pivotally rotated about pivot pin 24 and shaft means 32 is generally as follows. That is, as depicted in FIGS. 2 and 7, a worm shaft support block 140 is suitably fixedly secured as to the base member 14 and, in turn, journals a shaft means 142 fixedly carrying a worm shaft 144. One end of the shaft means 142 may be axially retained as by a washer member 146, secured as by an upset end portion 148 of shaft means 142, while the other axial end of shaft means 142 is secured to a knob 150 as by a press-fit pin member 152 effectively keying or locking the shaft means 142 to the knob 150.

As was previously described, block 36 (FIGS. 2 and 9) is secured, as by screws, to the platform base 46 and also, by virtue of pin or drive dog means 42 (FIG. 2) locked to the worm gear 34 for unitary motion therewith. Accordingly, if the adjustment knob 150 is rotated, for example, clockwise the resulting rotating worm shaft 144, engaged with worm gear 34, causes worm gear 34 to rotate in a clockwise direction (as viewed in either FIGS. 8 or 9). Since block 36 is correspondingly driven by worm gear 34, and secured to platform base 46, such rotation of worm gear 34 causes a swingable rotation of the platform base 46 and, in fact, the entire platform assembly 44. As a further consequence of such a swingable rotation (clockwise as viewed in either FIGS. 6 or 8), the free ends of locating arms 114 and 128 swing generally downwardly toward the plane 136.

If the adjustment knob 150 is rotated counterclockwise the resulting rotating worm shaft 144, engaged with worm gear 34, causes worm gear 34 to rotate in a counter-clockwise direction (as viewed in either FIGS. 8 or 9). Since block 36 is correspondingly driven by worm gear 34, and secured to platform base 46, such rotation of worm gear 34 causes a swingable rotation (counter-clockwise as viewed in FIGS. 6, 8 or 9) of the platform base 46 and, in fact, the entire platform assembly 44. As a further consequence of such a swingable rotation of the platform assembly 44, the free ends of locating arms 114 and 128 swing generally upwardly away from the plane 136.

As shown in FIGS. 1, 2, 3, 7 and 8, a support type block or bracket 154 is suitably fixedly secured to the frame means 12 as by screws 156 and 158 passing through block 154 and threadably engaging a portion of the support or leg 22. A driven bevel pinion gear 160, in meshed engagement with bevel gear 40, is fixedly secured to shaft means 162, for rotation therewith; the shaft means 162 is, in turn, journalled through support block or bracket 154 so as to extend therethrough and be, in turn, fixedly secured to a generally cylindrical dial 164 as by means of, for example, a set screw 166. A pointer or indicator 168 has its main body or base portion 170 fixedly secured as to the block or bracket 154 as by a screw 172. The dial 164 has a plurality of graduations 174 formed or carried on the outer cylindrical surface thereof. Such graduations 174 are also coded or, preferably, respectively identified with numerals. In one successful embodiment of the invention, the clockwise-most (as viewed in FIG. 9 or FIG. 2) graduation was identifisd as "16"; and in sequence, counter-clockwise therefrom, the succeeding graduations were respectively identified as: "15"; "14"; "13"; "12"; "11"; "10"; "9"; "8"; "7" and "6".

As previously described, rotation of knob 150 causes, as its ultimate purpose, the relative raising or lowering of the locators 120 and 134 (and the coaxial axes thereof). During such upward and downward movement of the locators 120 and 134, shaft means 32 is also undergoing rotation and such rotation is conveyed to bevel gear 40 which is in meshed engagement with the driven bevel gear 160. Also, as already described, bevel gear 160 is in operative fixed rotational engagement with the dial or indicator means 164. Consequently, if through such rotation of knob 150, the common axis of locators 120 and and 134 is brought to a then selected position, and, let it be assumed, the graduation (on the dial 164) juxtaposed to the pointer 168 reads "11", then this, in the preferred embodiment, indicates to the operator that the actual elevation, of the common axis of locators 120 and 134, is 11.0 cm. above the lower surface 180 of base plate 14. Similarly, if the juxtaposed graduation were either "6", "7", "8", "9", "10", "12", "13", "14", "15" or "16", such would indicate to the operator that the actual elevation or distance of the common axis, of locators 120 and 134, to the bottom or lower surface 180 of base plate 14 would be, respectively 6.0 cm., 7.0 cm., 8.0 cm., 9.0 cm., 10.0 cm., 12.0 cm., 13.0 cm., 14.0 cm., 15.0 cm. or 16.0 cm.

As already generally indicated, a clamp-like arm 38 is secured generally about shaft means 32 and tightened thereagainst, once a selected relationship in assembly is achieved, as by a screw 182. As a consequence, arm 38 rotates in direct unison with shaft means 32. A pointer adapter arm 184 (FIGS. 1, 3, 7, 8 and 9) is pivotally secured to clamp arm 38 as by a shoulder-type screw 186 which permits arm 184 to be pivotally rotated thereabout while still maintaining a selected axis of pivotal rotation. An abutment 188 carried by arm 38 serves as a stop against which the generally lower part of end-edge 190 of adapter arm 184 abuts when permitted to rotate clockwise about pivot 186. In order to provide for a degree of adjustment in order to assure that when adapter arm 184 is thusly in abutting engagement, that the axis of the aperture 192, formed in the free end thereof, is coaxial with the common axis of locators 120 and 134, a threaded member 194, such as a screw or the like, may be carried by the adapter arm 184 and threadably axially adjusted as to cause such member 194 to abut against stop 188 and, through such adjustment, attain the desired coaxial condition as among aperture 192 and locators 120 and 134. Obviously, adapter arm 184, through its connection to shaft 32 via clamp-like arm 38, rotates in unison with shaft 32, platform assembly 44 and locating arms 114 and 128.

At the left end, as viewed in FIGS. 1 and 2, a generally vertically upwardly extending plate or support member 198 is suitably fixedly secured to the frame means 12 as by, for example, a plurality of screws (not shown). As best seen in FIGS. 1 and 3, such support plate 198 may be comparatively rather narrow and is provided with a generally medially situated elongated slot 200. A clamp 202, which may be generally guided by the slot 200, is provided with a threaded passage portion 204 which threadably receives a threaded shank portion 206 of a manually actuatable knob 208. In the preferred embodiment, a cassette guide member 210 is secured to base plate 14, in spaced relationship to support 198, as by screws 212 and 214.

As possibly best shown in FIG. 2, the platform plate member 46 is provided with a clearance aperture or passageway 216 which permits the extension therethrough of a support post 218 which, at its lower end 220, may be located in a recess or counterbore 222 formed in base plate 14 and secured therein as by a screw 224. The upper end of post 218 is formed as with an extension 226 of relatively reduced diameter which serves as a pivotal pilot for one end of a swingable arm 228. A screw 230 serves to retain arm 228 onto the pilot portion 226 and operatively against the annular shoulder 232 without binding arm 228 and yet assuring that the arm 228 will pivot about pilot 226 in a constant plane parallel to surfaces 136 and 180. The swingable end of arm 228 is provided with an aperture 234 the axis of which, when the elements are in their respective depicted positions, passes through the common axis 236 of locators 120 and 134.

The movement and adjustment of locating arms 114 and 128, relative to each other, via gear racks 62 and 64 has already been disclosed. However, if it is desired that such a selected relative position be maintained, all that needs to be done is to rotate a locking knob 238 which, as best seen in FIGS. 4 and 5, has a threaded shank portion 240, threadably engaged with way member 54 and of a sufficient length as to enable such threaded shank portion to bear against the juxtaposed portion of gear rack 64 and thereby frictionally lock such gear rack 64 against further relative sliding action.

Although the practice of the invention is not so limited, in the preferred arrangement of the invention, elements 14, 16, 18, 138, 210, 218, 198, 202, 106, 104, 114, 128, 154, 120, 134, 68, 66, 238, 46, 54, 52, 56 and 58 are formed of a clear acrylic, while elements 62, 64, 20, 24, 26, 32, 36, 140 and 22 are formed of steel. Principally, for matter of weight clamping arm 38 is preferably formed of aluminum. The various gears are commercially available as stock items and the respective ratios etc. would, in the main, be a matter of personal choice.

In the use of the invention, one film cassette of unexposed film would be retained as at 250 (vertically generally between clamp 202 and the top of base plate 14 and generally laterally against support 198 by the clamp 202 at the top and the guide-like retainer member 210 at the bottom).

Further, in use, the apparatus is primarily intended to be set upon a table, portions of which are fragmentarily illustrated at 252 and 254. In such an arrangement, the height of the feet or risers 16 and 18 is such as to permit the very close reception, as between the table surface 256 and the underside surface 180 of base plate 14, of a second film cassette 258 of unexposed film so that, for all practical purposes the surface 180 will be the surface of the film to be exposed. Not only do the risers 16 and 18 provide for such a closely held vertical opening, but the inner sides thereof may well serve as longitudinal guides for the sliding guide of the film cassette being inserted therebetween.

OPERATION OF INVENTION

Figure 10:
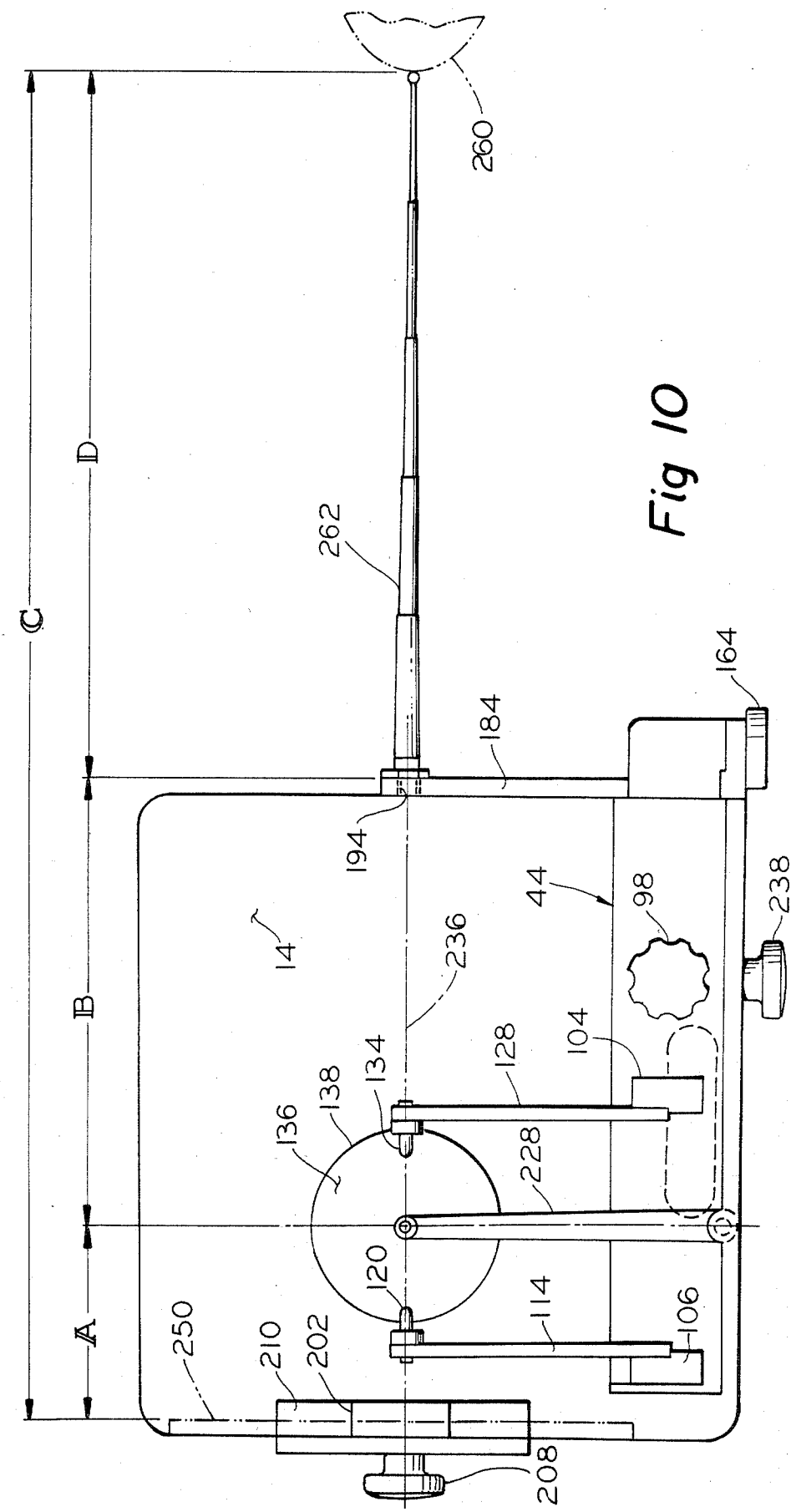
FIG. 10 is a view similar to that of FIG. 1, in reduced scale, and with considerably less detail, illustrating the apparatus of the invention as it may appear prior to the exposing of the unexposed film situated to the left of the patient's head.
Figure 11:
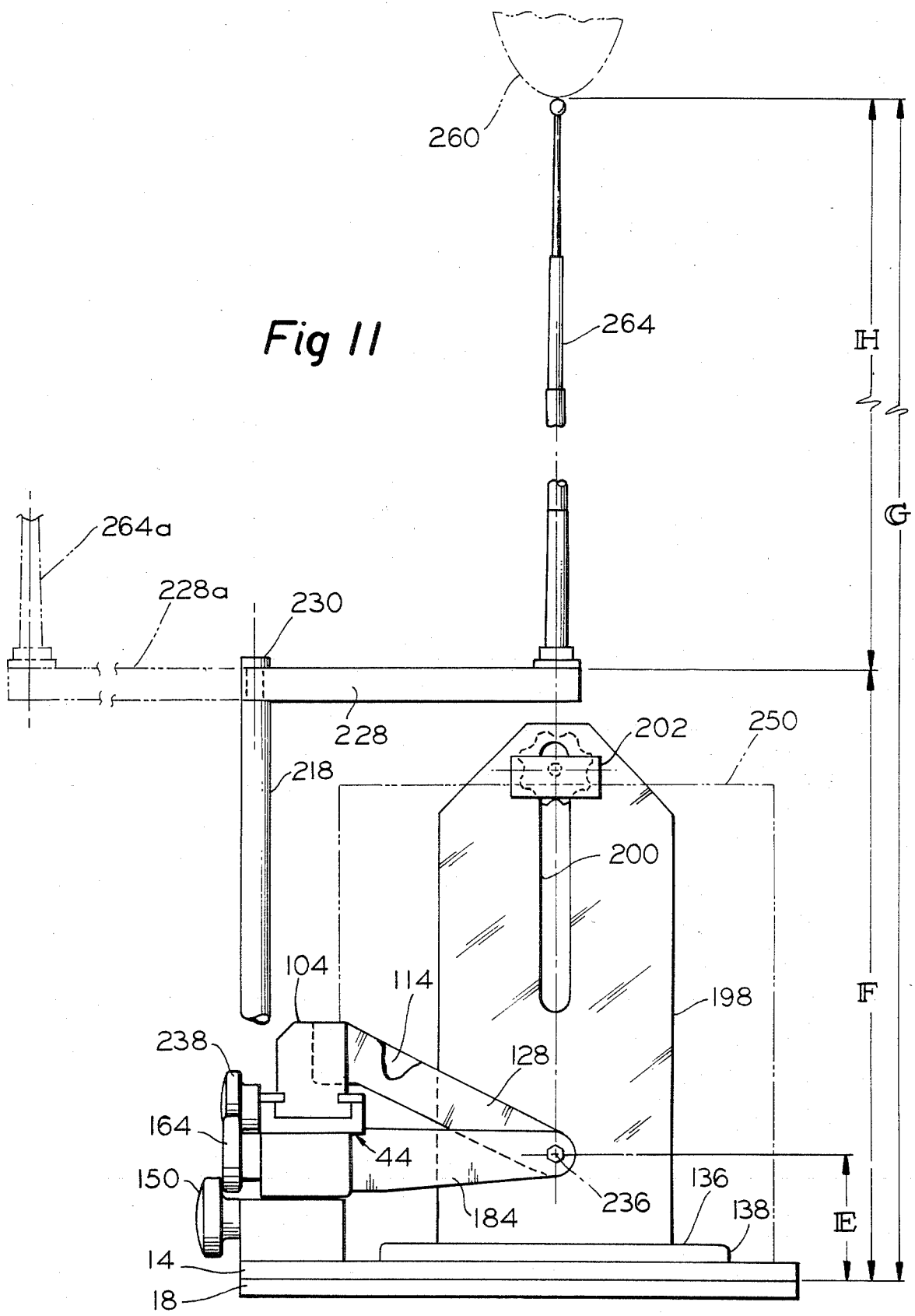
FIG. 11 is a view similar to that of FIG. 3, in reduced scale, and with considerably less detail, illustrating the apparatus of the invention as it may appear prior to the exposing of the unexposed film situated below the patient's head.

In order to better convey the operation of the invention in addition to FIGS. 1-9, reference will also be made to FIGS. 10 and 11.

FIGS. 10 and 11 are somewhat respectively similar to FIGS. 1 and 3 with the exceptions that FIGS. 10 and 11 are each of a relatively reduced scale and only so many of the elements (some somewhat comparatively simplistically illustrated) are shown as is believed necessary to convey the interrelationships thereof and the overall operation of the invention.

Referring in greater detail to FIGS. 10 and 11, in one successful embodiment of the invention, the mid-distance between the locating members 120 and 134 when measured to the plane of the cassette film to be exposed was established at a dimension, A, which, in the preferred embodiment was established to be 15.0 cm. Accordingly, after a patient's head is placed on the pad or riser 138 (preferably the elevation of which is sufficient to overcome the metal frame of the film cassette) as to have the back or posterior portion of that patient's head rest on surface 136, knob 98 is rotated in a direction as to cause the locating arms 114 and 128 as well as locating members 120 and 134 move relatively toward each other. The locating members 120 and 134 are in fact plug-like members adapted to be received in the external auditory canals, or porionic canals, of the patient. Therefore, such locating members 120 and 134 are moved generally inwardly toward the patient's auditory canals along with such adjustments as are necessary with knob 150 to place such locating members at the proper elevation to be properly received by the patient's auditory canals. When the proper elevation has thusly been selected and the proper distance inwardly of the patient's auditory canals by the locating members 120 and 134 has been achieved, the locking knob 238 may be turned as to lock the locating arms 114 and 128 and locators 120 and 134 in such a selected and proper position.

At this time certain factors are established; that is, the mid-sagittal plane of the patient has been established as existing parallel to the film in the cassette 250 and at a fixed dimension, A, away from the film of such cassette; the other is that the transporionic axis has also been established as being axially aligned with the axis 236 of the locating members 120 and 134 which is also coaxial with aperture means 192 of arm locator member 184.

In order to obtain a lateral X-ray exposure of the patient's head, all that is necessary is to bring the anode 260 of the related, generally standard, X-ray machine into alignment with axis 236 and cycle such X-ray machine for the desired exposure time. However, in many instances, it is desired to establish a particular degree of magnification which will be again used in subsequent cephlograms especially for purposes of comparison. With the invention this becomes very simple. That is, since the dimension, A, is fixed, the selected degree of magnification becomes a simple matter of mathematics. That is, the distance A+B+D (the total distance from the plane of the film to the anode 260 of the X-ray machine) divided by the distance B+D will give the resulting degree of magnification. Therefore, in the invention, with dimensions, A, and, B, being fixed and determined it becomes a simple mathematical equation to determine the dimension, D, in order to achieve the desired degree of magnification. This can be achieved as by the use of a telescoping rod 262 which is extensible and preferably detachably securable to the arm 184 as at threaded aperture 194. That is, with the axis of aperture 194 being aligned with axis 236 and the fixed dimensions, A and B, being known, all that has to be done is to attach telescoping rod 262 and extend it until it attains the proper calculated length, D, and then bring the anode 260 of the X-ray machine into alignment with rod 262 and in touching engagement therewith after which the arm 184 and telescoping rod 262 are swung upwardly (counter-clockwise as viewed in FIG. 8) and the X-ray machine cycled for the appropriate time span thereby exposing the film in the cassette 250.

Somewhat similarly, once the patient's head has been located as described above, the graduations on dial 164 are checked to see which of such graduations is, for example, juxtaposed to the pointer 168. If, for example, the juxtaposed graduation is "12", that would mean that dimension, E, is actually 12.0 cm. away from the plane of the film in the cassette 258. If it is desired to establish a particular degree of magnification which will be again used in subsequent cephlograms especially for purposes of comparison, such becomes a very simple mathematical equation with the invention. That is, since dimension, E , is established by virtue of the rotation of the platform means 44 and locators 120, 134, and therefore for that patient at that time, fixed, the selected degree of magnification becomes a simple matter of mathematics. That is, the distance H and F (the total distance from the plane of the film to the anode of the X-ray machine) divided by the distance G-E will give the resulting degree of magnification. Therefore, in the invention with dimension, F, being fixed and dimension, E, being determinable,it becomes a simple mathematical equation to determine the dimension, H, in order to achieve the desired degree of magnification. This can be achieved as by the use of a telescoping rod 264 which is extensible and detachably securable to the arm 228 at threaded aperture 234. That is, with the axis of aperture 234 being aligned with the mid-sagittal plane and fixed dimension, F, being known, less the determinable dimension, E, all that has to be done is to attach telescoping rod 264 and extend it until it attains the proper calculated length, H, and then bring the anode 260 of the X-ray machine into alignment with rod 264 and in touching engagement therewith after which the arm 228 and telescoping rod 264 may be swung as to a position depicted at 228a out of the line of action of the X-ray machine, and the X-ray machine cycled for the appropriate time span thereby exposing the film in the cassette 258.

As should be apparent, the invention provides an apparatus making it possible to obtain cephlograms, both lateral and anterior-posterior, of a patient regardless of the patient's age, physical infirmities or whether such patient is undergoing an operation.

FIG. 12, a view similar to a fragmentary portion of FIG. 2, illustrates a contemplated modification. Only so much of the structure is illustrated as is believed necessary to clearly teach the said contemplated modification and all elements shown in FIG. 12 which are like or similar to those of FIG. 2 are identified with like reference numbers. More particularly, in the embodiment of FIG. 12, it is contemplated that (instead of the guide or retainer means 210 of FIG. 2) the left-most (as viewed in FIG. 12) end of base plate 14 be cut or terminated as to define an end surface 270 effectively spaced from the vertical support 198 as to thereby be able to receive therebetween the lower portion of the X-ray film cassette means 250.

FIGS. 13 and 14 illustrate a gauging means 272 employable in combination with the structure of FIGS. 1–12. The gauging means 272 is illustrated as comprising opposed side walls 274 and 276 each of which may have a peripheral configuration as typically illustrated in FIG. 13 by side wall 276. That is, in FIG. 13, side wall 276 is depicted as preferably having opposed generally parallel side edges 278 and 280 each of which, at the left end thereof (as viewed in FIG. 13) terminate in an arcuate edge 282 and, at the right end thereof, terminate in an arcuate edge 284. In the preferred embodiment of the gauging means 272, the arcuate edges 282 and 284 are respective arcs of a radius, R, with the center of such radius being the mid point of the gauging means 272. Although not necessary to the practice of the invention, it is nevertheless preferred that the overall length, L, (L, being twice, R) of the gauging means 272, as measured at the medial axis 286 thereof, be of an easily "multipliable" number such as, for example, 10.0 cm. The two side walls 274 and 276, in turn, cooperate to, in effect, "sandwich" or contain therebetween a suitable radiographically opaque medium. It has been found that one such satisfactory opaque medium is barium sulfate and that in order to achieve the desired results all that is necessary is to paint-on a layer of such barium sulfate onto an inner surface of one of such side walls 274, 276 and to then affix the other side wall thereagainst. Other opaque mediums will, of course, be apparent to those of ordinary skill in the art and such other opaque mediums may be employed without departing from the teachings of the invention. In FIG. 14, the layer of radiographically opaque medium is depicted by the medially situated heavy line 288 which, for purposes of clarity, is greatly magnified in transverse thickness. As a consequence of applying the opaque medium 288 to the inner surface, the resulting peripheral configuration of such medium 288 preferably assumes that of the side wall 276 as depicted in FIG. 13.

The side walls 274 and 276 may in fact be physically integrally joined to each other and folded-over, as at an edge thereof, as to thereby be juxtaposed to each other and contain the opaque medium 288 therebetween, or, such may be physically separate walls, as depicted.

Such side walls 274 and 276 may be formed of any suitable material and it has been found that an inexpensive material, such as flat cardboard, provides totally acceptable results. The thickness of the cardboard (or other material forming walls 274 and 276) need only be sufficient to assure that the gauging means 272 maintain a generally flat configuration during use. In one successful embodiment of the gauging means 272, the walls 274 and 276 were constructed of pressed cardboard of a thickness in the order of 1/32 inch or 0.8 mm.

In the preferred embodiment, means are provided for operatively connecting the gauging means 272 to the structure of FIGS. 1–12 for cooperative action therebetween. In the embodiment of FIGS. 13 and 14, such mounting or connecting means takes the form of a mounting aperture 290 formed, through both side walls 274 and 276, with its center coincident with the center of radii, R. As will become apparent, the mounting aperture 290 is intended for preferably close or tight reception therein of components forming or carried by the structure of FIGS. 1–12.

The fragmentary portion of gauging means 272 of FIG. 15 illustrates a further modification wherein the mounting means comprises aperture means 290a (functionally similar to aperture means 290) which, in turn, comprises keying or polarizing means which, in the embodiment depicted, takes the form of a flatted surface 292.

FIG. 16 illustrates a fragmentary portion of the structure shown in FIG. 1 with such structure now being provided with the gauging means 272. It is contemplated, and such has been tested, that the gauging means 272 may be operatively mounted to the locating arm means 128 by pressing the gauging means 272 onto the outwardly projecting end 294, of the ear locating plug means 134, as to tightly receive such end 294 through mounting or aperture means 290.

FIG. 17, a view taken generally on the plane of line 17—17 of FIG. 16, looking in the direction of the arrows and rotated 90° out of its normal orthographic projection, illustrates the locating arm means 128 (and 114) along with the gauging or reference means 272 in varying positions of operation. More specifically, and for purposes of description, let it be assumed that the depicted solid-line relative position of locating arm means 128 and the corresponding position of reference or gauging means 272 represent the angular midpoint of the total angular travel (about the axis of journal means 24, 32, FIG. 2) of locating arm means 128 (and 114). Further, let it also be assumed that when the locating arm means 128 is positioned at its lower-most extreme, that such, along with gauging or reference means 272, is depicted by the dash-line portion of FIG. 17 with the elements thereof having reference numerals provided with a suffix "b". Also, let it be assumed that when the locating arm means 128 is positioned at its upper-most extreme, that such, along with gauging or reference means 272, is depicted by the dash-line portion of FIG. 17 with the elements thereof having reference numerals provided with a suffix "c".

As illustrated in FIG. 17, when the locating arm means 128 is situated in its midpoint, the longitudinal axis 286 is generally horizontal or parallel to the plane of the unexposed film (258 FIG. 2) situated below plate portion 14. Therefore, if at this time the X-ray machine 260, situated in a relationship as generally depicted in FIG. 11, is cycled, the radiographically opaque medium 288, of the gauging or reference means 272, being within the field of radiation of the X-ray machine, will cause a gauge or reference line to appear on the (exposed and) ultimately developed film. When such gauge or reference line on the developed film is measured, the length thereof, compared to the length, L, of the reference or gauging means 272, will determine the actual degree of magnification of the patient obtained. That is, if it is found that the gauging or reference line on the developed film measures, for example, 11.0 cm. and if the length, L, of the gauging or reference means 272 is 10.0 cm., then it becomes apparent that the degree of magnification (on the film) is ten percent (10%). Such a gauge or reference line produced on the developed X-ray film not only serves as a check to determine that the overall distance, G, has been properly selected (for the desired magnification) but also serves as a permanent record on the developed X-ray film for future reference.

When the locating arm means is lowered to its lower-most position, the gauging or reference means 272b also moves with such locating arm means. As is depicted, when the locating arm means 128b is in such lower-most position, the medial axis 286b is no longer parallel to the plane of the unexposed X-ray film below plate 14. However, because of the radially formed ends 282b and 284b, the effective length of such inclined gauging means 272b, measured parallel to the plane of the unexposed X-ray film below plate 14 and passing through axis 236b, is still equal to length, L. Therefore, if the X-ray machine 260, in a position depicted in FIG. 11, is cycled, the reference or gauge line produced on the exposed and developed film will still be an accurate indicator of the degree of magnification produced on the film.

It should now be apparent that the various elements perform in the same manner when the locating arm means 128 is moved to the upper-most position as depicted by the dash-line portion of FIG. 17 wherein the various elements are identified with reference numerals provided with a suffix "c".

In this connection, it should be pointed-out that the keying or indexing means 292 of the modification of FIG. 15, may be employed as in combination with an extension or projection 294 (FIGS. 16 and 17) which is provided with a coacting flatted surface positioned so as to result in the gauging means 272 being capable of being applied thereto only in a relationship resulting in that as depicted in FIG. 17; that is, being generally parallel to the plane of the X-ray film when the locating arm means 128 is in its midpoint of permissible travel. Of course, it should be apparent that the gauging or reference means 272 may be operatively affixed to the locating arm means 128 (or 114) by any suitable means even, for example, releasable adhesive means.

Because of the thinness of the layer of radiographically opaque material 288, as measured transversely of walls 274 and 276, there is no adverse effect on, for example, the X-ray film 250 (FIGS. 1, 2 and 3) in the event that the gauging means 272 remains on the locating arm means 128 (or 114) when the X-ray machine 260, in a position depicted in FIG. 10, is cycled to radiographically expose the film 250. However, because of the thickness of the layer of opaque material 288, as measured from edge 278 to edge 280, a gauge or reference line is produced when the direction of the X-ray radiation is generally from one of such edges 278 or 280 to the other of such edges 278 or 280. It has been found that a width of such layer of opaque material, as measured for example from edge 278 to 280, in the order of 3.0 cm. is sufficient to produce the desired resulting gauge or reference line on the exposed and developed X-ray film.

FIG. 18 illustrates fragmentary portions of the structure as shown in FIG. 3 along with the gauging or reference means 272. As seen in both FIGS. 18 and 19, the arm means 228 may be provided with suitable extension means 296 which, in turn, is closely or tightly received by aperture means 290 of gauging means 272.

The purpose of the gauging means 272, as illustrated in FIGS. 18 and 19, is the same as that disclosed by and described with reference to FIGS. 16 and 17. That is, with arm means 228 in the position shown in FIG. 18 and corresponding to the arrangement depicted in FIG. 10, when the X-ray machine 260 is cycled, the gauging or reference means 272 will create a gauge or reference line on the thusly exposed X-ray film 250 with such gauge or reference line having the same function as that previously described as appearing on the exposed (and developed) X-ray film 258.

Although only a preferred embodiment and certain modifications of the invention have been disclosed and described, it is apparent that other embodiments and modifications of the invention are possible within the scope of the appended claims.

What is claimed is:

1. A portable cephalostat, comprising portable body means, first means defining a non-resilient fixed reference plane of elevation carried by said body means and against which the back of a patient's head is to be directly located, second means for locating first unexposed film at a preselected elevation below the back of the patient's head and said fixed reference plate of elevation, third means for locating second unexposed film to one side of the patient's head when the back of said patient's head is located against said fixed reference plane of elevation and fourth means for guidingly positioning said patient's head along said fixed reference plane of elevation as to thereby have the mid-sagittal plane of said patient's head situated at a preselected distance from said second unexposed film and for determining the elevation above the plane of said first film of the axis of said patient's auditory canals when the mid-sagittal plane of the patient's head is at said preselected distance, wherein said second means comprises reference surface means carried by said body means, wherein said third means comprises support means carried by said body means, wherein said support means is effective to support said second unexposed film in a generally vertical position generally parallel to said mid-sagittal plane, wherein said fourth means comprises first and second arm-like means, first ear canal locating means carried by said first arm-like means and extending generally toward said second arm-like means, second ear canal locating means carried by said second arm-like means and extending generally toward said first arm-like means, said first and second arm-like means being adjustable through an arcuate path of movement simultaneously toward and away from said fixed reference plane of elevation as to enable said first and second ear canal locating means to be at an appropriate elevation with respect to said fixed reference plane of elevation as to enable the respective reception of said first and second ear canal locating means by the auditory canals of the patient's head, wherein said arcuate path of movement is about an axis of rotation, wherein said axis of rotation is parallel to said fixed reference plane of elevation, said first and second arm-like means also being simultaneously movable toward and away from each other as to thereby respectively generally contain and release said patient's head.

2. A cephalostat according to claim 1 and further comprising read-out type indicator means, said indicator means being effective to indicate the actual distance above said plane of said first film of the axis of the patient's auditory canals when the back of the patient's head is located against said fixed reference plane of elevation and the mid-sagittal plane of the patient's head is at said preselected distance.

3. A cephalostat according to claim 2 wherein said indicator means comprises dial means and readable dial-carried characters, said characters providing a visual indication of said distance above said plane of said first film when said first and second ear canal locating means are received by the patient's auditory canals.

4. A cephalostat according to claim 1 wherein said body means comprises additional support means, carrier means supported by said additional support means, wherein said carrier means is relatively rotatable with respect to said additional support means, wherein said first and second arm-like means are operatively carried by said carrier means as to be generally cantilevered therefrom, manually operative drive means carried by said carrier means, said manually operative drive means being operatively connected to said first and second arm-like means, said drive means being effective to cause said first and second arm-like means to simultaneouly move toward and away from each other, said manually operative drive means comprising rotary gear means, first gear rack means, second gear rack means, said first gear rack means being in meshed engagement with said rotary gear means at a generally first diametral side of said rotary gear means, said second gear rack means being in meshed engagement with said rotary gear means at a second diametral side of said rotary gear means generally opposite to said first diametral side, said first gear rack means being operatively connected to said first arm-like means, said second gear rack means being operatively connected to said second arm-like means, wherein upon manual rotation of said rotary gear means said first and second gear rack means are caused to move in directions opposite to each other, and wherein said first and second arm-like means is adjustable through said arcuate path of movement by rotation of said carrier means relative to said additional support means.

5. A cephalostat according to claim 4 and further comprising read-out type indicator means, said indicator means being continually responsive to the amount of rotation of said carrier means to thereby continually indicate the distance above said plane of said first film of the axis of said first and second ear canal locating means as said carrier means is undergoing rotation with respect to said additional support means.

6. A cephalostat according to claim 4 and further comprising second manually operative drive means, said second manually operative drive means comprising a first drive portion operatively carried by said carrier means and a second drive portion operatively carried by said body means, said first and second drive portions being effective to coact with each other as to cause selective rotation of said carrier means relative to said additional support means and said fixed reference plane of elevation, wherein said first drive portion comprises a first gear member operatively carried by said carrier means for movement in unison therewith, wherein said second drive portion comprises a second gear member, and whereby manual actuation of said second gear member causes movement of said first gear member and said relative rotation of said carrier means.

7. A cephalostat according to claim 4 and further comprising distance-gauging means for establishing the distance at which the anode of an associated X-ray machine should be positioned relative to the mid-sagittal plane of the patient's head, said distance gauging means comprising a lever arm operatively carried by said body means and pivotally rotatable with respect thereto, said lever arm being pivotally swingable into at least first and second positions, said lever arm being adapted to carry a variable-length rod-like means, wherein when said lever arm and variable-length rod-like means are collectively pivotally swung into said first position said variable-length rod-like means is in alignment with the axis of the patient's auditory canals when the back of said patient's head is against said fixed reference plane of elevation said first and second ear canal locating means are received by said patient's auditory canals and the mid-sagittal plane of the patient's head is at said preselected distance, and wherein when said lever arm and variable-length rod-like means are collectively pivotally swung into said second position said variable-length rod-like means is effectively beyond the area of radiation emitted by said X-ray machine, wherein said lever arm is pivotally connected to said carrier means as to be rotatable with respect thereto, and abutment means carried by said carrier means for operatively abutting against said lever arm and thereby determine said first position of said lever arm.

8. A cephalostat according to claim 1 and further comprising distance-gauging means for establishing the distance at which the anode of an associated X-ray machine should be positioned relative to the mid-sagittal plane of the patient's head, said distance gauging means comprising a lever arm operatively carried by said body means and pivotally rotatable with respect thereto, said lever arm being pivotally swingable into at least first and second positions, said lever arm being adapted to carry a variable-length rod-like menas, wherein when said lever arm and variable-length rod-like means are collectively pivotally swung into said first position said variable-length rod-like means is in alignment with the axis of the patient's auditory canals when the back of said patient's head is against said fixed reference plane of elevation said first and second ear canal locating means are received by said patient's auditory canals and the mid-sagittal plane of the patient's head is at said preselected distance, and wherein when said lever arm and variable-length rod-like means are collectively pivotally swung into said second position said variable-length rod-like means is effectively beyond the area of radiation emitted by said X-ray machine.

9. A cephalostat according to claim 1 and further comprising distance-gauging means for establishing the distance at which the anode of an associated X-ray machine should be positioned relative to a plane horizontal to said fixed reference plane of elevation and passing through the axis of the patient's auditory canals, said distance-gauging means comprising a lever arm operatively carried by said body means and pivotally rotatable with respect thereto, said lever arm being pivotally swingable into at least first and second positions, said lever arm being adapted to carry a variable-length rod-like means, wherein when said lever arm and variable-length rod-like means are collectively pivotally swung into said first position said variable-length rod-like means is in alignment with the mid-sagittal plane of the patient's head when the back of said patient's head is against said fixed reference plane of elevation said first and second ear canal locating means are received by said patient's auditory canals and the mid-sagittal plane of the patient's head is at said preselected distance, and wherein when said lever arm and variable-length rod-like means are collectively pivotally swung into said second position said variable-length rod-like means is effectively beyond the area of radiation emitted by said X-ray machine.

10. A cephalostat according to claim 1 and further comprising gauging means, said gauging means being effective to be in the path of radiation emitted by an associated X-ray machine as to result in a photographic image of said gauging means being produced on one of said films, wherein said gauging means comprises a thin layer of radiographically opaque medium, said layer being of a preselected length which is to serve as a gauge-length, said layer being of a thickness such as to present no detrimental interference to X-ray radiation passing therethrough, and said layer being of a width as to present a significant interference to the passage of X-ray radiation in a direction generally through said width.

11. A cephalostat according to claim 10 wherein said gauging means is operatively carried by at least one of said arm-like means.

12. A cephalostat according to claim 10 wherein said layer of radiographically opaque medium comprises barium sulfate.

13. A cephalostat according to claim 10 wherein said layer of radiographically opaque medium comprises barium sulfate painted onto a surface of a radiographically permeable body member.

* * * * *

UNITED STATES PATENT AND TRADEMARK OFFICE
CERTIFICATE OF CORRECTION

PATENT NO. : 4,566,444
DATED : January 28, 1986
INVENTOR(S) : John L. Spolyar

It is certified that error appears in the above-identified patent and that said Letters Patent is hereby corrected as shown below:

Column 1, line 35, after "cephlograms" delete "grams".
Column 7, line 12, change "identifised" to --identified--.
Column 14, Claim 1, line 13, change "plate" to --plane--.
Column 14, Claim 1, line 17, after "elevation" add a comma (,).
Column 16, Claim 8, line 23, after "rod-like" change "menas" to
--means--.

Signed and Sealed this

Sixth Day of May 1986

[SEAL]

Attest:

DONALD J. QUIGG

Attesting Officer     Commissioner of Patents and Trademarks